United States Patent [19]

Murai et al.

[11] 4,024,280

[45] May 17, 1977

[54] ABIETANILIDES, THEIR PRODUCTION AND USE

[75] Inventors: Hiromu Murai, Otsu; Katsuya Ohata, Uji; Hiroshi Enomoto, Kyoto; Kenji Sempuku, Suita; Koji Kitaguchi, Joyo; Yukio Fujita, Takatsuki; Yoshiaki Yoshikuni; Kohei Kura, both of Kyoto; Katsuhide Saito, Joyo; Tamiki Mori, Yokaichi; Yasuo Yasutomi, Takatsuki, all of Japan

[73] Assignee: Nippon Shinyaku Co., Ltd., Japan

[22] Filed: May 12, 1975

[21] Appl. No.: 576,360

[30] Foreign Application Priority Data

May 14, 1974 Japan .............................. 49-54093

[52] U.S. Cl. .............................. 424/324; 260/557 B

[51] Int. Cl.² .............. A61K 31/165; C07C 102/00; C07C 103/37

[58] Field of Search .................... 424/324; 260/557

[56] References Cited

UNITED STATES PATENTS 2,201,237  5/1940  Littman .............................. 260/97

OTHER PUBLICATIONS

Organic Chemistry, Fieser & Fieser, 3rd Ed., (1960), D. C. Heath and Company, Boston, pp. 178–179.

Primary Examiner—Frederick E. Waddell

[57] ABSTRACT

Process for the preparation of abietanilides which comprises reacting abietic acid, dihydroabietic acid, tetrahydroabietic acid or a reactive derivative thereof with aniline and the products thereby produced, compositions containing the same for reducing blood serum cholesterol and method of use of such compositions.

11 Claims, No Drawings

ABIETANILIDES, THEIR PRODUCTION AND USE

DETAILED DESCRIPTION OF THE INVENTION

This invention relates to new abietanilide compounds, i.e. diterpenic acid anilides such as abietanilide (hereinafter referred to as "AAN"), dihydroabietanilide (hereinafter referred to as "DAN") and tetrahydroabietanilide (hereinafter referred to as "TAN") and procedure for their preparation. More particularly, the invention relates to a process for the preparation of diterpenic acid anilides such as AAN, DAN and TAN which comprises reacting a diterpenic acid such as abietic acid (hereinafter referred to as "AA"), dihydroabietic acid (hereinafter referred to as "DA") and tetrahydroabietic acid (hereinafter referred to as "TA") or a reactive derivative thereof such as an acid anhydride, an ester or an acid halide with aniline to obtain corresponding diterpenic acid anilides. The invention also comprises the abietanilides thus produced in compositions for blood serum cholesterol reduction and the administration thereof for reducing blood serum cholesterol levels in subjects having hypercholesterolemia.

In carrying out the invention, a dehydrating agent represented by a dicycloalkyl-dicarboxydiimide and a basic catalyst represented by a hydroxide, alkoxide or amide of an alkakli metal may be used.

These abietanilides (such as AAN, DAN and TAN) prepared according to the process of this invention have high activity in reducing blood serum cholesterol levels and are thus very valuable as anti-arteriosclerotic agents.

Diterpenic acids useful as starting compounds in this invention are readily available. Specifically, AA is a naturally occurring compound which is contained in large quantities in resins of plants belonging to the family Pinaceae and is readily available at low cost. Furthermore, DA and TA can easily be obtained by reacting AA with a suitable reducing agent.

Conversion of diterpenic acids into reactive derivatives such as their acid anhydrides, esters and acid halides are performed according to customary procedures. More specifically, acid anhydrides are generally formed by using dehydrating agents such as acetic anhydride and acetyl chloride; esters are formed by conventional esterification methods such as methylation with diazomethane and acid halides are formed by halogenation using such halogenating agents as $PX_5$, $PX_3$ and $SOX_2$ (in which X is a halogen atom such as chlorine).

As solvents for the reaction, there can be employed alcohols such as methanol and ethanol, aliphatic and aromatic hydrocarbons such as n-hexane, benzene and xylene, halogenated hydrocarbons such as chloroform, cyclic ethers such as dioxane and tetrahydrofuran, and aromatic heterocyclic compounds such as pyridine.

Starting compounds are generally charged in such amounts that 1.1 to 3 moles of aniline is used per mole of the diterpenic acid or its derivative, for example, its acid anhydride, ester or acid halide. At the charging of the starting compounds, if desired, a suitable amount of the acid component may be charged in the dissolved state or suspended in a solvent and the amine may be added little by little to the solution or suspension under cooling and agitation, if necessary.

The reaction is carried out appropriately under ice cooling, at room temperature or under heating and it is generally completed within several hours. Completion of the reaction can easily be confirmed by disappearance of spots of the starting substances by silica gel thin layer chromatography using a developing agent such as chloroform.

After completion of the reaction, the desired diterpenic acid anilide such as AAN, DAN and TAN can be isolated from the reaction mixture according to any customary method. For example, when a reaction solvent miscible with water is employed, the solvent is removed from the reaction mixture under reduced pressure and a water-immiscible solvent such as ether or benzene is added to the residue. In this case, use of chloroform is not preferred because an emulsion is readily formed when a chloroform layer containing AAN, DAN, TAN or the like is shaken with water and this emulsion is so stable that a long time is required for completion of the liquid-liquid separation. In case a water-immiscible solvent such as benzene or n-hexane is employed, the reaction mixture is washed, according to need, with a dilute acid of a concentration of 3 to 5%, a dilute aqueous solution containing 3 to 5% of an alkali and then with water and dried, and when the solvent was removed from the washed layer, the desired product is obtained generally in the form of fine crystals or a crystalline powder. In this case, decoloration is performed by treatment with activated carbon, if necessary. Recrystallization is conducted by using a recrystallization solvent. In case the residue left after removal of the solvent is an oily product, purification is performed by alumina or silica gel column chromatography or preparative thin layer chromatography.

DA used in this invention is $\Delta^8$dihydroabietic acid, but DA that can be employed for the synthesis of the anilide is not limited to the $\Delta^8$-dihydro-compound since the $\Delta^7$-, $\Delta^{13}$- and $\Delta^{14}$-isomers are intended to be included in the scope of this invention.

The invention will now be described in detail by reference to the following non-limitative Examples.

EXAMPLE 1

Preparation of Abietanilide (AAN)

2.93 g (5 millimoles) of AA anhydride was dissolved in 30 ml of ethanol, and 0.93 g (10 millimoles) of aniline was added little by little to the solution. The liquid mixture was heated and refluxed under agitation for 5 hours and the ethanol was removed under reduced pressure. The oily residue was dissolved in 100 ml of ether and the solution was washed with 3% KOH aqueous solution, water, 3% HCl and water in this order. The ether layer was dried over anhydrous magnesium sulfate and the ether was removed to give 1.33 g of oily residue (the yield being 70.7%). The product was developed with chloroform by using a preparative silica gel thin layer (manufactured by Merck; the thickness being 2 mm) and extracting with chloroform containing 30% of methanol to effect purification. There was thus obtained a colorless glassy substance.

CONH (KBr): 1650 cm$^{-1}$ and 3250 cm$^{-1}$

Elementary Analysis Values as $C_{26}H_{35}ON$: Calculated: C = 82.71%, H = 9.34%, N = 3.71% Found: C = 82.90%, H = 9.28%, N = 3.86%

EXAMPLE 2

Preparation of $\Delta^8$-Dihydroabietanilide ($\Delta^8$-DAN)

4.77 g (15 millimoles) of $\Delta^8$-DA methyl ester prepared from $\Delta^8$-DA and excess diazomethane and 4.19 g (45 millimoles) of aniline were mixed in 100 ml of xylene, and b 1.95 g (50 millimoles) of sodium amide was added to the liquid mixture. The mixture was heated and refluxed under agitation for 30 hours. The reaction mixture was cooled and filtered, and the xylene layer as the filtrate was washed with 5% HCl and water and dried over anhydrous magnesium sulfate. Xylene was removed under reducedpressure and the crystalline powder residue was recrystallized from ethanol to give 3.45 g of colorless needles melting at 150.5° to 151.5° C ( the yield being 60.7%).

Elementary Analysis Values as $C_{26}H_{37}ON$: Calculated: C = 82.27%, H = 9.83%, N = 3.69% Found: C = 82.40%, H = 9.81%, N = 3.89%

EXAMPLE 3

Preparation of Tetrahydroabietanilide (TAN)

2.33 g (25 millimoles) of aniline was added under ice cooling to a solution of b 3.25 g (10 millimoles) of TA chloride prepared from TA and excess thionyl chloride in 10 ml of pyridine, and the mixture was agitated under ice cooling for 30 minutes. After completion of the reaction, pyridine was removed under reduced pressure and 100 ml of ether was added to the residue. The mixture was washed with 5% HCl, water and 3% NaOH aqueous solution in this order, and the ether layer was dried over anhydrous magnesium sulfate and the ether was removed. The residual crystalline powder was recrystallized from ethanol to give 3.15 g of colorless prisms melting at 143° to 145° C (the yield being 83.7%).

Elementary Analysis Values as $C_{26}H_{39}ON$: Calculated: C = 81.83%, H = 10.30%,, N = 3.67% Found: C = 81.96%, H = 10.24%, N = 3.83%

EXAMPLE 4

Preparation of $\Delta^8$-dihydroabietanilide ($\Delta^8$-DAN)

3.04 g (10 millimoles) of $\Delta^8$-DA was dissolved in 50 ml of dioxane, and b 2.47 g (12 millimoles) of dicyclohexylcarbodiimide was added to the solution under agitation at room temperature. The mixture was agitated for 30 minutes and 1.02 g (11 millimoles) of aniline was added dropwise to the mixture at room temperature. The liquid mixture was agitated for 2 hours at room temperature and for 30 minutes at 60° C. The reaction mixture was concentrated under reduced pressure to remove dioxane, and 100 ml of methylene chloride was added to the oily residue. The methylene chloride layer was washed with 3% HCl and water, dried over anhydrous magnesium sulfate and filtered. The filtrate was concentrated so that the volume was reduced to 25 ml, and the concentrate was allowed to stand quiescent at room temperature overnight. The precipitate was removed by filtration and the filtrate was concentrated to dryness. The powdery residue was recrystallized from ethanol to give 2.21 g of colorless needles melting at 150° to 151° C (the yield being 58.3%).

Elementary Analysis Values as $C_{26}H_{37}ON$: Calculated: C = 82.27%, H = 9.83%, N = 3.69% Found: C = 82.31%, H = 9.76%, N = 3.80%

The $\Delta^7$-, $\Delta^{13}$- and $\Delta^{14}$- dihydroabietanilides are prepared in analogous or in the same manner as the process of Example 2 or 4.

Compounds prepared according to this invention have high activity for reducing cholesterol in blood, which can be proved by an experiment described below and hence are useful in the treatment of hypercholesterolemia in mammals or subjects having the same.

A completely synthetic diet containing 1% of cholesterol, 0.25% of sodium cholate and 0.003%, 0.01%, 0.03% and 0.1% of the test compound is given to a group of 6 male rats having a body weight of about 50 g consecutively for 3 days, and the rats are fasted overnight. Then, the rats are decapitated and their blood collected to determine the cholesterol concentration in the blood. The concentration of cholesterol in the blood is measured with Technicon Autoanalyzer (Technicon Laboratory: Method File N-24a). The results obtained are shown in Table 1.

Table 1

| Compound | % Inhibition Dose in Diet | | | |
|---|---|---|---|---|
| | 0.003% | 0.01% | 0.03% | 0.1% |
| $\Delta^8$-Dihydro-abietanilide | 18 | 22 | 56* | 93* |

Each value shown in the Table is a relative value determined based on the supposition that the value of the control group (the cholesterol-administered group) is 0 and the value of the normal group (the non-cholesterol-administered group) is 100. The mark "*" indicates that the value is statistically significant over the control group with a significance level of 1%.

From the results shown in the Table, it will readily be understood that each compound has a significant effect in reducing cholesterol in blood even when it is administered in a very minute amount and is very valuable as an anti-arteriosclerotic agent. The active abietanilide is administered to the mammal or subject in any suitable or known manner, if desired, in combination with a pharmaceutically acceptable carrier or vehicle.

What is claimed is:

1. A diterpenic acid anilide selected from the group consisting of abietic acid anilide, dihydroabietic acid anilide, and tetrahydroabietic acid anilide.

2. A compound of claim 1 which is abietic acid anilide.

3. The compound of claim 1 which is a dihydroabietic acid anilide.

4. The compound of claim 3 which is $\Delta^8$-, $\Delta^7$-, $\Delta^{13}$- or $\Delta^{14}$-dihydroabietic acid anilide.

5. The compound of claim 1 which is tetrahydroabietic acid anilide.

6. A composition useful for the reduction of blood serum cholesterol which comprises an effective amount of a diterpenic acid anilide according to claim 1 and a pharmaceutically acceptable carrier.

7. A composition according to claim 6 wherein the diterpenic acid anilide is abietic acid anilide.

8. A composition according to claim 6 wherein the diterpenic acid anilide is a dihydroabietic acid anilide.

9. A composition according to claim 6 wherein the diterpenic acid anilide is $\Delta^8$-, $\Delta^7$-, $\Delta^{13}$- or $\Delta^{14}$-dihydroabietic acid anilide.

10. A composition according to claim 6 wherein the diterpenic acid anilide is tetrahydroabietic acid anilide.

11. A method of reducing blood serum cholesterol in a mammal which comprises orally administering to said mammal an effective amount of a a diterpenic acid anilide according to claim 1.

* * * * *